United States Patent [19]

Cahoy

[11] 4,152,329

[45] May 1, 1979

[54] 2-ACYLAMINOTHIAZOL-4-YLACETAMIDES AS POST-EMERGENT SELECTIVE HERBICIDES

[75] Inventor: Roger P. Cahoy, Overland Park, Kans.

[73] Assignee: Gulf Oil Corporation, Pittsburgh, Pa.

[21] Appl. No.: 839,688

[22] Filed: Oct. 5, 1977

Related U.S. Application Data

[62] Division of Ser. No. 743,542, Nov. 22, 1976, Pat. No. 4,120,690.

[51] Int. Cl.² .................................... C07D 277/20
[52] U.S. Cl. .......................... 260/306.8 R; 71/90
[58] Field of Search .............................. 260/306.8 R

[56] References Cited

U.S. PATENT DOCUMENTS

| | | | |
|---|---|---|---|
| 3,505,055 | 4/1970 | Von Schmeling et al. | 71/90 |
| 3,547,917 | 9/1970 | Kulka et al. | 71/90 |
| 3,821,239 | 6/1974 | Guillot et al. | 260/306.8 R |
| 3,862,167 | 1/1975 | Venu et al. | 260/306.8 R |

*Primary Examiner*—Nicholas S. Rizzo
*Attorney, Agent, or Firm*—Carl A. Cline

[57] ABSTRACT

A class of amides disclosed to be useful as selective post-emergent herbicides are those having the general structural formula

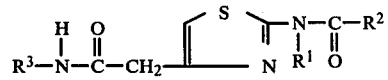

in which $R^1$ is hydrogen or lower alkyl, $R^2$ is amino, lower alkyl, lower chloroalkyl, lower alkylamino, lower alkenylamino, lower alkoxy or $C_3$ to $C_5$ cycloaklyl and $R^3$ is phenyl, thiazolyl, thiadiazolyl or lower alkyl-substituted, halogen-substituted or trifluoromethyl-substituted phenyl, thiazolyl or thiadiazolyl.

13 Claims, No Drawings

2-ACYLAMINOTHIAZOL-4-YLACETAMIDES AS POST-EMERGENT SELECTIVE HERBICIDES

This is a division of U.S. Ser. No. 743,542, filed Nov. 22, 1976, now U.S. Pat. No. 4,120,690.

DESCRIPTION OF THE INVENTION

Ali et al. in *The Journal of Chemical and Engineering Data*, vol. 17, p. 106 (1972) reported that 4-bromoacetoacetanilide and thiourea in refluxing ethanol yielded the corresponding 2-aminothiazole hydrobromide. Treatment with ammonium hydroxide yielded 50% 2-aminothiazol-4-ylacetic acid anilide, m.p. 152°–54°.

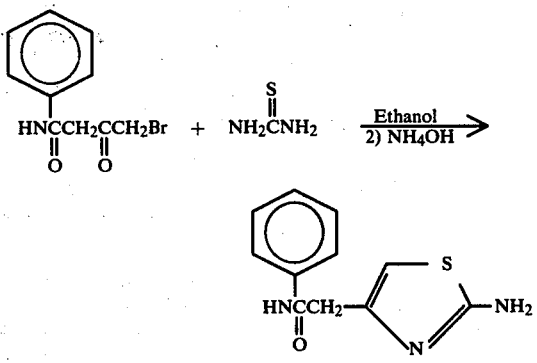

This general class of aminothiazolylacetanilides, including compounds with various substituents on the phenyl ring are non-phytotoxic and in fact appear to have no effect on plant life at all. I have discovered, however, that when an acyl or carbamoyl substituent is attached to the free amino group, the resulting compounds are useful, selective post-emergent herbicides. This class of herbicides also includes amides and ureas derived from various nitrogen containing heterocyclic bases as well as those derived from aniline and substituted anilines, as discussed below.

SYNTHESIS OF THE HERBICIDES

The starting materials employed in synthesis of the compounds of this invention are various acetoacetamides derived from aniline, substituted anilines and various heterocyclic nitrogen bases. These compounds may be prepared by reacting amines which have replaceable hydrogen with ethyl acetoacetate or diketene or an approximately 50 percent acetone solution of diketene. Bromination of the acetoacetamides in acetic acid reaction medium produces almost exclusively the corresponding 4-bromoacetoacetamides. The latter compounds are stable intermediates which react with thiourea or N-substituted thiourea in the presence of an acid scavenger in ethanol reaction medium to give the corresponding amino-thiazolylacetamides in good yields. Reaction with various available acylating agents or alkyl isocyanates then yields the herbicides of this invention. Illustrative synthesis procedures are exemplified below.

PREPARATION OF 3'-TRIFLUOROMETHYLACETOACETANILIDE

A two-liter reaction flask fitted with a magnetic stirrer, heating mantle, dropping funnel, thermometer, water-cooled condenser and Dean Stark trap was charged with 156.2 g (1.2 moles) of ethyl acetoacetate and 400 ml of xylene. The dropping funnel contained 161 g (1.0 mole) of 3-aminobenzotrifluoride and 320 ml xylene. The solution in the reaction pot was heated to 135° and the contents of the dropping funnel were added dropwise over a period of three hours. The low-boiling liquid which accumulated in the Dean Stark trap was periodically drained in order to maintain a reaction temperature of about 135°. After four hours, the reaction was judged to be completed and the reaction solution was cooled. There was added 650 ml of hexane. Cooling in an ice bath yielded a white crystalline precipitate. The product was collected on a vacuum filter and dried in an oven. There was obtained 136.6 g (55.7%) of 3'-trifluoromethylacetoacetanilide, m.p. 109°–10°. N.M.R. (CDCl$_3$) δ 2.2 (CH$_3$, keto), 3.5 (CH$_2$), 7.2–7.9 (aromatic), 1.8 (CH$_3$, enol).

PREPARATION OF 4-BROMO-3'-TRIFLUOROMETHYLACETOACETANILIDE

A one-liter reaction flask equipped with a mechanical stirrer, air-cooled condenser, thermometer and dropping funnel was charged with 290 ml of acetic acid and 167.3 g (0.68 mole) of 3'-trifluoromethylacetoacetanilide. Only a portion of the latter dissolved. The dropping funnel contained 108.8 g (0.68 mole) of bromine, a crystal of iodine and 65 ml of acetic acid. The pot mixture was stirred as the bromine solution was added dropwise while maintaining the reaction temperature at 20°–25°. The reaction solids appeared to dissolve and reprecipitate as the bromine addition was continued. When about 65% of the bromine solution had been added, a clear reaction solution was obtained. All material remained in solution when the remaining quantity of bromine solution was added. The reaction solution was allowed to stir overnight at ambient temperature. On the following morning, the solidified mass was added to 2.8 liters of cold water and stirred. The white solid was collected on a vacuum filter and the filter cake was washed with an additional one liter of water. After drying, there was obtained 210 g (95%) of 4-bromo-3'-trifluoromethylacetoacetanilide, m.p. 66°–8°. N.M.R. (CDCl$_3$)

δ 3.8 (—CCH$_2$C—), 4.0 (—CCH$_2$Br), 5.3 (CH, enol), 7.2–7.8 (aromatic), 9.0 (HNC=O).

PREPARATION OF 2-(TRIMETHYLACETAMIDO)-4-(3-TRIFLUOROMETHYLPHENYLCARBAMOYLMETHYL)THIAZOLE

A 500 ml reaction flask fitted with a magnetic stirrer, heating mantle, thermometer and water-cooled condenser was charged with 44.7 g (0.138 mole) of 4-bromo-3'-trifluoromethylacetoacetanilide, 350 ml of absolute ethanol and 15 g (0.19 mole) of pyridine. A 26 g - sample (0.162 mole) of N-trimethylacetylthiourea [m.p. 140°–42°; prepared as described by Moore and Crossley in *The Journal of the American Chemical Society*, vol. 62, p. 3273 (1940)] was added to the reaction solution. As the substituted thiourea dissolved, the reaction temperature increased from 24° to 31°. The solution was refluxed for four hours and poured into 1.5 liters of water. With stirring, the residual oil crystallized. The product was collected and washed with water. There was obtained 46.8 g (88%) of white solid, m.p. 147°–52°.

One recrystallization from ethyl acetate - heptane yielded material which melted at 153°-55°. N.M.R. (dimethyl-d$_6$ sulfoxide) ∂ 1.3 (tert-butyl), 3.8 (CH$_2$), 6.9 (hetero-aromatic), 7.3-8.1 (aromatic).

PREPARATION OF 4-(3-TRIFLUOROMETHYLPHENYLCARBAMOYLMETHYL)-2-UREIDO THIAZOLE

Thiobiuret (4.3 g, 0.036 mole) which had been prepared as described by Klayman et al. in *The Journal of Organic Chemistry*, vol. 37, p. 1536 (1972), 4-bromo-3'trifluoromethylacetanilide (11.3 g, 0.035 mole), pyridine (4.0 g, 0.05 mole) and 100 ml of absolute ethanol were refluxed for three hours. The solvent was removed under reduced pressure and the residual solid was stirred with water. The collected product was dried and recrystallized from ethyl acetate-hexane. There was obtained 6.2 g of the desired product, m.p. 195°-97°. N.M.R. (dimethyl-d$_6$ sulfoxide) ∂ 3.6 (CH$_2$), 6.8 (heteroaromatic), 7.3-8.0 (aromatic and NH).

PREPARATION OF 2-AMINO-4-(3-TRIFLUOROMETHYLPHENYLCARBAMOYLMETHYL)THIAZOLE

A solution of 31.1 g (0.096 mole) of 4-bromo-3'-trifluoromethylacetoacetanilide in 130 ml of absolute ethanol was carefully mixed with 8.4 g (0.11 mole) of thiourea. As the thiourea dissolved, the temperature of the solution increased from 23° to 38°. After the exothermic reaction had subsided, the solution was refluxed for four hours and poured into 130 ml of water. A small quantity of insoluble material was removed by filtration and the filtrate was made basic (pH 9) with ammonium hydroxide. Stirring and cooling yielded a crystalline solid which was collected. There was obtained 19 g (65.7%) of dry product, m.p. 116°-18°. N.M.R. (dimethyl-d$_6$ sulfoxide) ∂ 3.4 (CH$_2$), 6.3 (hetero-aromatic), 6.8 (NH$_2$), 7.3-8.0 (aromatic), 10.3 (HNC=O).

PREPARATION OF 2-(3-METHYLUREIDO)-4-(3-TRIFLUOROMETHYLPHENYLCARBAMOYLMETHYL)-THIAZOLE

A solution of 10 g (0.033 mole) of 2-amino-4-(3-trifluoromethylphenylcarbamoylmethyl)thiazole, and 2.3 g (0.04 mole) of methyl isocyanate in 50 ml of pyridine was heated at 50° for three hours. The reaction solution was mixed with 400 ml of water and allowed to stand overnight in the refrigerator. On the following morning, the crystalline solid was collected and dried in the oven. There was obtained 10 g of the desired product, m.p. 200°-203°. N.M.R. (dimethyl-d$_6$ sulfoxide) ∂ 2.7-2.8 (CH$_3$, doublet), 6.8 (hetero-aromatic), 7.3-8.1 (aromatic), 10.4 (HNC=O).

PREPARATION OF 2-ACETOXYAMINO-4-(3-TRIFLUOROMETHYLPHENYLCARBAMOYLMETHYL)THIAZOLE

To a solution of 5.0 g (0.017 mole) of 2-amino-4-(3-trifluoromethylphenylcarbamoylmethyl)thiazole in 22 ml of pyridine, there was added dropwise 2.8 g (0.03 mole) of methyl chloroformate. The solution was stirred and heated at 40°-45° for eighteen hours. The mixture was poured into 300 ml of cold water and stirring induced crystal formation. The solid was collected and the filter cake was washed with water. There was obtained 4.9 g of product, m.p. 137°-40°. N.M.R. (dimethyl-d$_6$ sulfoxide) ∂ 3.6-3.9 (OCH$_3$, CH$_2$), 6.8 (hetero-aromatic), 7.3-8.1 (aromatic), 10.4 (HNC=O).

PREPARATION OF 2-METHYLAMINO-4-(3-TRIFLUOROMETHYLPHENYLCARBAMOYLMETHYL)THIAZOLE

A solution containing 32.4 g (0.10 mole) of 4-bromo-3'-trifluoromethylacetoacetanilide and 11.3 g (0.13 mole) of N-methylthiourea in 250 ml of ethanol was refluxed for four hours. The reaction mixture was poured into 700 ml of water and ethanol was added. A small quantity of insoluble material was removed by filtration and the filtrate was made strongly alkaline by the addition of ammonium hydroxide. The solution was cooled and an additional 400 ml of water was added. The precipitated solid was collected and dried in an oven. There was obtained 25.5 g (81%) of product, m.p. 153°-55°. N.M.R. (dimethyl-d$_6$ sulfoxide) ∂ 2.8-2.9 (CH$_3$, doublet), 3.5 (CH$_2$), 6.3 (hetero-aromatic), 7.3-8.1 (aromatic, NH), 10.4 (HNC=O).

PREPARATION OF 2-(1,3-DIMETHYLUREIDO)-4-(3-TRIFLUOROMETHYLPHENYLCARBAMOYLMETHYL)THIAZOLE

A solution comprising 12.7 g (0.04 mole) of 2-methylamino-4-(3-trifluoromethylphenylcarbamoylmethyl)thiazole, 3.1 g (0.054 mole) of methyl isocyanate in 40 ml of pyridine was heated at about 45° for 24 hours. The reaction solution was poured into water and the crude product was collected. Two recrystallizations from isopropanolheptane yielded 7.1 g of desired product, m.p. 125°-27°. N.M.R. (dimethyl-d$_6$ sulfoxide) ∂ 2.8 (CH$_3$, doublet), 3.5 (CH$_3$, singlet), 3.8 (CH$_2$), 6.9 (hetero-aromatic), 7.3-8.1 (aromatic), 10.4 (HNC=O).

PREPARATION OF 2-(N-ISOBUTYRYL-N-METHYLAMINO)-4-(3-TRIFLUOROMETHYLPHENYLCARBAMOYLMETHYL)THIAZOLE

A solution containing 7.6 g (0.025 mole) of 2-methylamino-4-(3-trifluoromethylphenylcarbamoylmethyl)thiazole and 2.9 g (0.027 mole) of isobutyryl chloride in 25 ml of pyridine was heated at about 45° for 24 hours. The mixture was poured into water. The thick oil failed to crystallize. The aqueous phase was decanted and the residue was dissolved in benzene. The organic phase was washed with water, dried over sodium sulfate and cooled. With stirring, hexane was added and a crystalline product precipitated. There was obtained 5.8 g of the desired amide, m.p. 122°-23°. N.M.R. (dimethyl-d$_6$ sulfoxide) ∂ 1.1-1.3 (2×CH$_3$), 2.7-3.4 (CH, septet), 3.6 (NCH$_3$), 3.7 (CH$_2$), 6.9 (hetero-aromatic), 7.3-8.1 (aromatic), 10.4 (HNC=O).

PREPARATION OF 2-AMINO-5-TERT-BUTYL-1,3,4-THIADIAZOLE

A three-liter reaction flask fitted with a power stirrer, heating mantle, dropping funnel, thermometer and water-cooled condenser was charged with 449 g (4.4 moles) of pivalic acid and 1500 ml of dioxane. To the stirred solution there was added 364 g (4.0 moles) of thiosemicarbazide. The dropping funnel was charged with 765 g (5.0 moles) of phosphorus oxychloride which was added to the well stirred solution in the reaction vessel. The reaction mixture was stirred and heated at 95°-100°. When the evolution of hydrogen chloride was complete, the mixture was cooled and the liquid phase was removed by decantation. Sufficient hot water was added to dissolve the pot residue. With ice-bath cooling and agitation, there was slowly added 450 ml of 50% aqueous sodium hydroxide. The mixture was cooled to 20° and the product was collected on a vacuum filter. The filter cake was washed with water and dried. There was obtained 404 g (64.2%) of 2-amino-5-tert-butyl-1,3,4-thiadiazole, m.p. 187°–88°.

PREPARATION OF N-(5-TERT-BUTYL-1,3,4-THIADIAZOL-2-YL)ACETOACETAMIDE

A two-liter reaction flask with appropriate fittings was charged with 33.6 g (0.4 mole) of diketene, 965 ml of xylene and 59.7 g (0.38 mole) of 2-amino-5-tert butyl-1,3,4-thiadiazole. The stirred mixture was heated to 70° at which time all solids had dissolved. After one hour, the solution was cooled and added to 2500 ml of chilled heptane. Product precipitation was judged complete after two hours. The solids were collected on a vacuum filter and air dried. There was obtained 54 g (58.9%) of white product, m.p. 166°–68°. N.M.R. (CDCl$_3$-dimethyl-d$_6$ sulfoxide) ∂ 1.5 [C(CH$_3$)$_3$], 2.0 (CH$_3$, enol), 2.3 (CH$_3$, keto), 3.6 (CH$_2$), 5.4 (CH, enol).

PREPARATION OF N-(5-TERT-BUTYL-1,3,4-THIADIAZOL-2-YL)-4-BROMOACETOACETAMIDE

A reaction flask was charged with 14.3 g (0.059 mole) of N-(5-tert-butyl-1,3,4-thiadiazol-2-yl)acetoacetamide dissolved in 230 ml of acetic acid. With efficient stirring, there was added dropwise 9.4 g (0.059 mole) of bromine dissolved in 55 ml of acetic acid while controlling the temperature at 20°–25°. The reaction solution was allowed to stir overnight at ambient temperature. On the following morning a sample of the precipitated solids was withdrawn. By N.M.R. analysis, the material was determined to be the corresponding 2-bromoacetoacetamide, m.p. 128°–30°. The reaction mixture was heated at 75°–80° for twelve hours. The solution was cooled to 20° and the precipitated solid was collected on a vacuum filter. After washing the filter cake with water, the material was stirred with aqueous sodium bicarbonate. The product was isolated and dried. There was obtained 8.8 g (46.6%) of authentic N-(5-tert-butyl-1,3,4-thiadiazol-2-yl)-4-bromoacetoacetamide, m.p. 144°–46°. N.M.R. (CDCl$_3$) ∂ 1.4 [C(CH$_3$)$_3$], 4.4 (CH$_2$), 6.3 (CH, enol).

PREPARATION OF 4-(5-TERT-BUTYL-1,3,4-THIADIAZOL-2-YLCARBAMOYLMETHYL)-2-AMINOTHIAZOLE

A reaction mixture comprising 11.2 g (0.035 mole) of N-(5-tert-butyl-1,3,4-thiadiazol-2-yl)-4-bromoacetoacetamide, 200 ml of ethanol and 2.8 g (0.037 mole) of thiourea was refluxed for three hours. The reaction solution was cooled and added to 300 ml of water. With stirring, there was slowly added an excess of saturated aqueous sodium bicarbonate. The product was collected and dried. There was obtained 10 g (96.2%) of white solid, m.p. 226° (dec.). N.M.R. (dimethyl-d$_6$ sulfoxide) ∂ 1.4 [C(CH$_3$)$_3$], 3.6 (CH$_2$), 6.3 (hetero-aromatic), 6.9 (NH).

PREPARATION OF 4-(5-TERT-BUTYL-1,3,4-THIADIAZOL-2-YLCARBAMOYLMETHYL)-2-METHYLAMINOTHIAZOLE

A reaction mixture containing 11.4 g (0.035 mole) of N-(5-tert-butyl-1,3,4-thiadiazol-2-yl)-4-bromoacetoacetamide, 150 ml of ethanol and 3.3 g (0.036 mole) of N-methylthiourea was refluxed for four hours. The reaction solution was poured into 300 ml of water and treated with excess aqueous sodium bicarbonate. The product was isolated and dried. There was obtained 9.5 g (87.2%) of white solid, m.p. 198°–200° (dec.). N.M.R. (CDCl$_3$) ∂ 1.4 [C(CH$_3$)$_3$], 3.0 (CH$_3$), 3.8 (CH$_2$), 6.4 (hetero-aromatic).

PREPARATION OF 4-(5-TERT-BUTYL-1,3,4-THIADIAZOL-2-YLCARBAMOYLMETHYL)-2-(3-METHYLUREIDO)-THIAZOLE

A reaction mixture comprising 3.0 g (0.01 mole) of 4-(5-tert-butyl-1,3,4-thiadiazol-2-ylcarbamoylmethyl)-2-aminothiazole, 50 ml of pyridine and 0.8 g (0.014 mole) of methyl isocyanate was heated at 35°–37° for four hours. The reaction solution was allowed to stand over the weekend at ambient temperature. Most of the pyridine was removed by employing a rotary evaporator. The residue was mixed with hexane and the crude solid was collected. The filter cake was well washed with ethyl acetate. There was obtained 2.5 g of product, m.p. 190° (dec.). N.M.R. (dimethyl-d$_6$ sulfoxide) ∂ 1.4 [C(CH$_3$)$_3$], 2.6 (CH$_3$, doublet), 3.7 (CH$_2$), 6.7 (hetero-aromatic).

PREPARATION OF 4-(5-TERT-BUTYL-1,3,4-THIADIAZOL-2-YLCARBAMOYLMETHYL)-2-PROPIONAMIDOTHIAZOLE

A mixture of 4.8 g (0.016 mole) of 4-(5-tert-butyl-1,3,4-thiadiazol-2-ylcarbamoylmethyl)-2-aminothiazole dissolved 20 ml of propionic anhydride was heated for one hour at 90°. The reaction solution was cooled and the precipitate was collected. The crude solid was recrystallized from chloroform-hexane. There was obtained 1.9 g of product, m.p. 210°–12°. N.M.R. (CDCl$_3$) ∂ 1.1–1.4 (CH$_3$, triplet), 1.4 [C(CH$_3$)$_3$], 2.3–2.7 (CH$_2$, quartet), 3.9 (CH$_2$, singlet), 6.8 (hetero-aromatic).

PREPARATION OF 4-(5-TERT-BUTYL-1,3,4-THIADIAZOL-2-YLCARBAMOYLMETHYL)-2-(1,3-DIMETHYLUREIDO)-THIAZOLE

A 4.0 g sample (0.013 mole) of 4-(5-tert-butyl-1,3,4-thiadiazol-2-ylcarbamoylmethyl)-2-methylaminothiazole was dissolved in 30 ml of pyridine and 1.1 g (0.02 mole) of methyl isocyanate was added. The solution was stirred and heated at 50° for twelve hours. Water was added and the mixture was stirred for two hours at ice-bath temperatures. After most of the oil-like material had crystallized, the product was collected and washed with water. There was obtained 3.2 g of white solid, m.p. 175°–77°. N.M.R. (CDCl$_3$) ∂ 1.5 [C(CH$_3$)$_3$], 2.7–2.9 (CH$_3$, doublet), 3.4 (CH$_3$, singlet), 4.1 (CH$_2$), 6.9 (hetero-aromatic).

Compounds which have been synthesized by means of the illustrated method are listed in the following table.

Compounds of the General Structural Formula

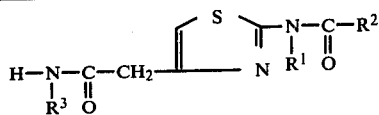

| Compound No. | R¹ | R² | R³ | M.P. (°C.) |
|---|---|---|---|---|
| 1 | H | allylamino | phenyl | 178–181 |
| 2 | H | cyclopropyl | phenyl | 203–207 |
| 3 | H | ethyl | phenyl | 177–179 |
| 4 | H | tert-butyl | phenyl | 190–192 |
| 5 | methyl | methylamino | phenyl | 167–170 |
| 6 | methyl | ethylamino | phenyl | 117–120 |
| 7 | methyl | allylamino | phenyl | 114–116 |
| 8 | methyl | methylamino | p-chlorophenyl | 214–217 |
| 9 | methyl | cyclopropyl | p-chlorophenyl | 140–143 |
| 10 | H | ethyl | p-methoxyphenyl | 173(dec.) |
| 11 | H | cyclopropyl | m-chlorophenyl | 215–218 |
| 12 | methyl | cyclopropyl | m-chlorophenyl | 127–130 |
| 13 | methyl | methylamino | m-chlorophenyl | 144–147 |
| 14 | H | isopropyl | m-chlorophenyl | 164–166 |
| 15 | H | tert-butyl | m-chlorophenyl | 161–163 |
| 16 | H | methyl | m-chlorophenyl | 172–174 |
| 17 | H | 1-pentyl | m-chlorophenyl | 125–127 |
| 18 | H | 2,2-dimethylpropyl | m-chlorophenyl | 143–146 |
| 19 | H | 3-pentyl | m-chlorophenyl | 140–142 |
| 20 | H | ethyl | m-chlorophenyl | 163–165 |
| 21 | methyl | ethylamino | m-chlorophenyl | 88–91 |
| 22 | H | 2-chloromethyl-isopropyl | m-chlorophenyl | 141–143 |
| 23 | H | ethyl | 3,4-dichlorophenyl | 154–157 |
| 24 | methyl | 3,4-dichlorophenyl | 188–191 | |
| 25 | H | 2-methylpropyl | 3,4-dichlorophenyl | 165–167 |
| 26 | H | isopropyl | 3,4-dichlorophenyl | 187–189 |
| 27 | H | 1-pentyl | 3,4-dichlorophenyl | 109–112 |
| 28 | H | tert-butyl | 3,4-dichlorophenyl | 191–193 |
| 29 | H | 3-pentyl | 3,4-dichlorophenyl | 172–173 |
| 30 | H | methyl | 3,4-dichlorophenyl | 102 |
| 31 | methyl | methylamino | o-chlorophenyl | 107–110 |
| 32 | methyl | methylamino | p-tolyl | 191–193 |
| 33 | methyl | ethyl | p-tolyl | 103–110(dec.) |
| 34 | H | ethyl | m-trifluoromethylphenyl | 152–154 |
| 35 | H | cyclopropyl | m-trifluoromethylphenyl | 178–181 |
| 36 | H | methylamino | m-trifluoromethylphenyl | 200–203 |
| 37 | H | tert-butyl | m-trifluoromethylphenyl | 153–155 |
| 38 | H | 3-pentyl | m-trifluoromethylphenyl | 133–134 |
| 39 | H | isopropyl | m-trifluoromethylphenyl | 174–175 |
| 40 | H | 2-methylpropyl | m-trifluoromethylphenyl | 147–149 |
| 41 | methyl | methylamino | m-trifluoromethylphenyl | 125–127 |
| 42 | methyl | isopropyl | m-trifluoromethylphenyl | 122–123 |
| 43 | H | ethylamino | m-trifluoromethylphenyl | 187–189 |
| 44 | H | propylamino | m-trifluoromethylphenyl | 161–163 |
| 45 | H | methoxy | m-trifluoromethylphenyl | 137–140 |
| 46 | H | 2-chloromethyl-isopropyl | m-trifluoromethylphenyl | 137–139 |
| 47 | H | amino | m-trifluoromethylphenyl | 195–197 |
| 48 | H | isopropyl | p-iodophenyl | 197–199(dec.) |
| 49 | H | isopropyl | m-iodophenyl | 172–174 |
| 50 | H | cyclopropyl | m-fluorophenyl | 235–236 |
| 51 | H | isopropyl | m-fluorophenyl | 186–188 |
| 52 | H | ethyl | 4-bromo-3-methylphenyl | 180–182 |
| 53 | H | ethyl | m-bromophenyl | 156–159 |
| 54 | H | isopropyl | m-bromophenyl | 188–190 |
| 55 | H | ethyl | 2,6-dimethylphenyl | 190–192 |
| 56 | H | ethyl | 3-chloro-4-methylphenyl | 153–155 |
| 57 | H | tert-butyl | 4-biphenylyl | 176–177 |
| 58 | H | ethyl | 3,5-dichlorophenyl | 222–224 |
| 59 | H | ethyl | 4-methyl-2-thiazolyl | 173–176(dec.) |
| 60 | H | methyl | 4-methyl-2-thiazolyl | 200(dec.) |
| 61 | H | methyl | 5-tert-butyl-1,3,4-thiadiazol-2-yl | 190(dec.) |
| 62 | H | ethyl | 5-tert-butyl-1,3,4-thiadiazol-2-yl | 210–212 |
| 63 | methyl | methylamino | 5-tert-butyl-1,3,4-thiadiazol-2-yl | 190(dec.) |
| 64 | H | isopropyl | 5-tert-butyl-1,3,4-thiadiazol-2-yl | 55(dec.) |
| 65 | H | ethyl | 5-tert-butyl-1,3,4-thiadiazol-2-yl | 58–60 |

Compounds of the General Structural Formula

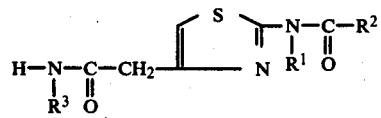

| Compound No. | R¹ | R² | R³ | M.P. (°C.) |
|---|---|---|---|---|
| 66 | methyl | ethylamino | 5-trifluoromethyl-1,3,4-thiadiazol-2-yl | 187–188 |
| 67 | methyl | methylamino | 5-trifluoromethyl-1,3,4-thiadiazol-2-yl | 223(dec.) |
| 68 | H | methyl | 5-trifluoromethyl-1,3,4-thiadiazol-2-yl | 212–214(dec.) |
| 69 | H | tert-butyl | 5-trifluoromethyl-1,3,4-thiadiazol-2-yl | 183–185 |
| 70 | H | isopropyl | 5-trifluoromethyl-1,3,4-thiadiazol-2-yl | 160–163 |

SELECTIVELY COMBATING UNWANTED VEGETATION

The novel herbicides are particularly effective when used post-emergently against broad-leaved weeds in grain fields. Greenhouse tests are described below to illustrate selective post-emergent use.

PROCEDURE

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The species of plants on which each compound was tested were planted in disposable plastic pots in a greenhouse. Ten to eighteen days after emergence of the plants, three pots of each species were sprayed at each application rate with an aqueous dispersion of the active compound prepared as described above, at rates of both 1 lb. and 3 lb. of active compound per acre and at a spray volume of 40 gal. per acre. Approximately one week after the spray application the plants were observed and phytotoxicity was rated according to the following schedule.

0 - NO CONTROL OR INJURY
1 - 1 TO 25 PERCENT CONTROL OR INJURY
2 - 26 TO 75 PERCENT CONTROL OR INJURY
3 - 76 TO 99 PERCENT CONTROL OR INJURY
4 - COMPLETE CONTROL OR KILL

Post-Emergent Phytotoxicity Results
Plant Species

| Compound No. | Rate (lb/A.) | Cockle burr | Lambs-quarter | Morning-glory | Pigweed | Wild Buckwheat | Wild Mustard | Alfalfa | Cotton | Peanut | Soybean | Corn | Grain Sorghum | Rice | Wheat | Oats | Radish | Sugar beets |
|---|---|---|---|---|---|---|---|---|---|---|---|---|---|---|---|---|---|---|
| 1 | 3 | 4 | 3 | 4 | 2 | 4 | 4 | 3 | 2 | 0 | 1 | 1 | 0 | 2 | 0 | | | |
|   | 1 | 2 | 2 | 4 | 0 | 0 | 4 | 0 | 0 | 0 | — | 0 | 0 | 0 | 0 | | | |
| 2 | 3 | 4 | 4 | 4 | 2 | 4 | 4 | 4 | 1 | 0 | 4 | 1 | 0 | 2 | 0 | | | |
|   | 1 | 4 | 4 | 4 | 2 | 4 | 4 | 0 |   | 0 | — | 0 | 0 | 0 | 0 | | | |
| 3 | 3 | 4 | 4 | 4 | 4 | 4 | 4 | 4 | 4 | 0 | 4 | 1 | 2 | 3 | 1 | | | |
|   | 1 | 4 | 4 | 4 | 4 | 4 | 3 | 4 | 3 | 0 | 4 | 0 | 0 | 0 | 0 | | | |
| 4 | 3 | 4 | 4 | 3 | 4 | 4 | 4 | 2 | 2 | 0 | 1 | 0 | 0 | 0 | 0 | | | |
|   | 1 | 1 | 4 | 1 | 1 | 4 | 4 | 1 | 1 | 0 | 1 | 0 | 0 | 0 | 0 | | | |
| 5 | 3 | 4 | 4 | 4 | 4 | 4 | 4 | 3 | 4 | 0 | 2 | 1 | 1 | 2 | 0 | | | |
|   | 1 | 4 | 4 | 3 | 4 | 4 | 4 | 3 | 2 | 0 | 1 | 0 | 0 | 0 | 0 | | | |
| 6 | 3 | 3 | 4 | 2 | 4 | 4 | 4 | 3 | 3 | 0 | 1 | 0 | 0 | 0 | 0 | | | |
|   | 1 | 1 | 4 | 2 | 4 | 4 | 4 | 1 | 1 | 0 | 1 | 0 | 0 | 0 | 0 | | | |
| 7 | 3 | 2 | 4 | 2 | 4 | 4 | 4 | 2 | 2 | 0 | 1 | 1 | 0 |   | 0 | | | |
|   | 1 | 0 | 4 | 1 | 4 | 1 | 4 | 1 | 1 | 0 | 1 | 0 | 0 | 0 | 0 | | | |
| 8 | 3 | 4 | 4 | 4 | 4 | 4 | 4 | 3 | 4 | 1 | 2 | 1 | 1 | 3 | 1 | | | |
|   | 1 | 3 | 4 | 4 | 3 | 4 | 4 | 1 | 2 | — | — | 0 | 0 | 2 | 0 | | | |
| 9 | 3 | 4 | 4 | 3 | 4 | 4 | 4 | 4 | 0 | 0 | 1 | 0 | 0 | 4 | 1 | | | |
|   | 1 | 4 | 4 | 4 | 3 | 4 | 3 | 1 | 0 | 0 | — | 0 | 0 | 2 | 0 | | | |
| 10 | 3 | 3 | 4 | 1 | 4 | 4 | 4 | 2 | 3 | 1 | 2 | 0 | 0 | 2 | 0 | | | |
|    | 1 | 0 | 4 | 0 | 2 | 1 | 4 | 3 | 1 | 0 | 1 | 0 | 0 | 3 | 0 | | | |
| 11 | 3 | 4 | 4 | 1 | 2 | 4 | — | 3 | 2 | 0 | 1 | 0 | 0 | 2 | 0 | | | |
|    | 1 | 3 | 4 | 1 | 1 | 1 | 4 | 2 | 1 | 0 | 1 | 0 | 0 | 0 | 0 | | | |
| 12 | 3 | — | — | — | 1 | 4 | 4 | 2 | 1 | 0 | 0 | 0 | 0 | 2 | 0 | | | |
|    | 1 | 4 | 4 | 2 | 1 | 0 | 4 | 0 | 0 | 0 | 1 | 0 | 0 | 4 | 0 | | | |
| 13 | 3 | 4 | 4 | 2 | 3 | 4 | 4 | 2 | 4 | 1 | 4 | 0 | 0 | 3 | 0 | | | |
|    | 1 | 4 | 4 | 0 | 3 | 4 | 4 | 3 | 3 | 0 | 0 | 0 | 0 | 0 | 0 | | | |
| 14 | 3 | 4 | 4 | 3 | 3 | — | 4 | 4 | 4 | 0 | 4 | 0 | 0 | 1 | 1 | | | |
|    | 1 | 4 | 4 | 2 | 3 | — | 4 |   | 1 | 0 | 2 | 0 | 0 | 2 | 0 | | | |
| 15 | 3 | 4 | 4 | 3 | 3 | 4 | 4 | 4 | 4 | 0 | 2 | 0 | 0 | 2 | 1 | | | |
|    | 1 | 4 | 4 | 2 | 0 | — | 4 | 3 | 0 | 0 | 1 | 0 | 0 | 3 | 0 | | | |
| 16 | 3 | 4 | 4 | 3 | 4 | 4 | 4 | 4 | 4 | 0 | 4 | 0 | 0 | 2 | 0 | | | |
|    | 1 | 4 | 4 | 3 | 3 | 4 | 4 | 4 | 4 | 0 | 4 | 0 | 0 | 1 | 0 | | | |
| 17 | 3 | 4 | 4 | 3 | 2 | 4 | 4 | 1 | 0 | 0 | 0 | 0 | 2 | 0 |   | | | |

-continued

Post-Emergent Phytotoxicity Results
Plant Species

| Compound No. | Rate (lb/A.) | Cockle burr | Lambs- quarter | Morning- glory | Pig- weed | Wild Buck- wheat | Wild Mus- tard | Al- falfa | Cot- ton | Pea- nut | Soy- bean | Corn | Grain Sor- ghum | Rice | Wheat | Oats | Rad- ish | Sugar beets |
|---|---|---|---|---|---|---|---|---|---|---|---|---|---|---|---|---|---|---|
|  | 1 | 2 | 4 | 2 | 2 | 4 | 4 | 1 | 0 | 0 | 0 | 0 | 0 | 1 | 0 |  |  |  |
| 18 | 3 | 0 | 4 | 1 | 2 | 4 | 4 | 0 | 0 | 0 | 0 | 0 | 0 | 1 | 0 |  |  |  |
|  | 1 | 0 | 4 | 0 | 1 | 4 | 4 | 0 | 0 | 0 | 0 | 0 | 0 | 1 | 0 |  |  |  |
| 19 | 3 | 2 | 4 | 4 | 4 | 4 | 4 | 3 | 2 | 0 | 0 | 0 | 0 | 4 | 1 |  |  |  |
|  | 1 | 1 | 4 | 3 | 1 | 4 | 4 | 2 | 0 | 0 | 0 | 0 | 0 | 1 | 0 |  |  |  |
| 20 | 3 | 4 | 4 | 4 | 4 | 2 | 4 | 3 | 2 | 0 | -4 | 0 | 0 | 4 | 1 |  |  |  |
|  | 1 | 4 | 4 | 3 | 4 | 4 | 4 | 2 | 3 | 0 | 4 | 0 | 0 | 3 | 1 |  |  |  |
| 21 | 3 | 4 | 4 | 2 | 3 | 4 | 4 | 4 | 2 | 0 | 1 | 0 | 1 | 0 | 0 |  |  |  |
|  | 1 | 4 | 2 | 2 | 4 | 0 | 4 | 2 | 0 | 0 | 0 | 0 | 0 | 0 | 0 |  |  |  |
| 22 | 3 | 4 | 4 | 3 | 3 | — | 4 | 3 | 2 | 0 | 1 | 0 | 0 | 0 | 0 |  |  |  |
|  | 1 | 2 | 4 | 2 | 1 | — | 3 | 1 | 0 | 0 | 0 | 0 | 0 | 0 | 0 |  |  |  |
| 23 | 3 | 4 | 4 | 3 | 2 | 4 | — | 4 | 3 | 1 | 2 | 0 | 0 | 2 | 2 |  |  |  |
|  | 1 | 2 | 4 | 1 | 2 | 4 | 4 | 2 | 3 | 2 | 1 | 0 | 0 | 2 | 1 |  |  |  |
| 24 | 3 | — | 4 | 1 | 2 | 4 | — | 2 | 3 | 1 | 4 | 0 | 0 | 3 | 0 |  |  |  |
|  | 1 | 4 | 4 | 1 | 2 | 4 | 4 | 1 | 1 | 1 | 1 | 0 | 0 | 1 | 0 |  |  |  |
| 25 | 3 | 2 | 4 | 2 | 2 | 4 | 4 | 2 | 4 | 0 | 1 | 0 | 0 | 3 | 1 |  |  |  |
|  | 1 | 2 | 4 | 1 | 2 | 4 | 4 | 0 | 3 | 0 | 0 | 0 | 0 | 1 | 0 |  |  |  |
| 26 | 3 | 4 | 4 | 3 | 4 | 4 | 4 | 3 | 4 | 0 | 2 | 0 | 0 | 3 | 2 |  |  |  |
|  | 1 | 4 | 4 | 4 | 4 | 4 | 4 | 1 | 3 | 0 | 2 | 0 | 0 | 2 | 0 |  |  |  |
| 27 | 3 | 2 | 4 | 2 | 3 | 4 | 4 | 1 | 2 | 0 | 0 | 0 | 0 | 2 | 0 |  |  |  |
|  | 1 | 0 | 4 | 1 | 2 | 4 | 3 | 0 | 1 | 0 | 0 | 0 | 0 | 1 | 0 |  |  |  |
| 28 | 3 | 4 | 4 | 2 | 3 | 4 | 4 | 2 | 3 | 0 | 1 | 0 | 0 | 3 | 0 |  |  |  |
|  | 1 | 4 | 4 | 2 | 2 | 4 | 3 | 1 | 3 | 0 | 2 | 0 | 0 | 0 | 0 |  |  |  |
| 29 | 3 | 2 | 4 | 2 | 4 | 4 | 4 | 2 | 2 | 0 | 1 | 0 | 0 | 3 | 0 |  |  |  |
|  | 1 | 1 | 4 | 2 | 2 | 4 | 3 | 1 | 1 | 0 | 1 | 0 | 0 | 1 | 0 |  |  |  |
| 30 | 3 | 4 | 4 | 3 | 4 | 4 | 4 | 4 | 4 | 2 | 4 | 0 | 0 | 1 | 3 |  |  |  |
|  | 1 | 4 | 4 | 1 | 1 | 4 | 4 | 2 | 3 | 2 | 3 | 0 | 0 | 1 | 2 |  |  |  |
| 31 | 3 | 0 | 4 | 0 | 4 | 4 | 4 | 2 | 3 | 0 | 0 | 0 | 0 | 1 | 0 |  |  |  |
|  | 1 | 0 | — | 0 | 4 | 4 | 2 | 1 | 1 | 0 | 0 | 0 | 0 | 1 | 0 |  |  |  |
| 32 | 3 | 3 | 4 | 2 | 4 | — | — | 3 | 3 | 0 | 3 | 0 | 0 | 3 | 1 |  |  |  |
|  | 1 | 2 | 4 | 1 | 4 | 4 | 2 | 2 | 1 | 0 | 2 | 0 | 0 | 1 | 0 |  |  |  |
| 33 | 3 | 4 | 4 | 1 | 4 | — | — | 0 | 1 | 0 | 2 | 0 | 0 | 2 | 0 |  |  |  |
|  | 1 | 0 | 4 | 0 | 4 | 4 | 4 | 0 | 1 | 0 | 0 | 0 | 0 | 1 | 0 |  |  |  |
| 34 | 3 | 4 | 4 | 4 | — | 4 | 4 | 4 | 4 | 1 | 4 | 0 | 0 | 3 | 2 |  |  |  |
|  | 1 | 4 | 4 | 3 | 4 | — | 4 | 4 | 4 | 1 | 4 | 0 | 0 | 3 | 1 |  |  |  |
| 35 | 3 | 4 | 4 | 4 | 4 | 4 | 4 | 4 | 4 | 1 | 4 | 0 | 0 | 3 | 1 |  |  |  |
|  |  | 4 | 4 | 4 | 4 | 4 | 4 | 4 | 4 | 1 | 1 | 0 | 0 | 1 | 0 |  |  |  |
| 36 | 3 | 4 | 4 | 4 | 4 | 4 | 4 | 4 | 4 | 0 | 2 | 0 | 1 | 3 | 1 |  |  |  |
|  | 1 | 2 | 4 | 2 | 4 | 4 | 4 | 4 | 2 | 0 | 1 | 0 | 0 | 2 | 1 |  |  |  |
| 37 | 3 | 4 | 4 | 4 | 4 | 4 | 4 | 4 | 3 | 0 | 3 | 0 | 0 | 1 | 1 |  |  |  |
|  | 1 | 4 | 4 | 3 | 2 | 4 | 4 | 2 | 2 | 0 | 4 | 0 | 0 | 1 | 1 |  |  |  |
| 38 | 3 | 4 | 4 | 4 | 4 | 4 | 4 | 3 | 2 | 0 | 1 | 0 | 0 | 1 | 0 |  |  |  |
|  | 1 | 2 | 4 | 2 | 0 | 2 | 4 | 2 | 1 | 0 | 1 | 0 | 0 | 0 | 0 |  |  |  |
| 39 | 3 | 4 | 4 | 4 | 4 | 4 | 4 | 4 | 4 | 1 | 4 | 0 | 0 | 4 | 1 |  |  |  |
|  | 1 | 4 | 4 | 4 | 4 | 4 | 4 | 4 | 4 | 1 | 3 | 0 | 0 | 3 | 0 |  |  |  |
| 40 | 3 | 4 | 4 | 3 | 4 | 4 | 4 | 4 | 1 | 0 | 1 | 0 | 0 | 3 | 0 |  |  |  |
|  | 1 | 4 | 4 | 3 | 4 | 0 | 4 | 2 | 1 | 1 | 0 | 0 | 0 | 1 | 0 |  |  |  |
| 41 | 3 | 4 | 4 | 4 | 4 | 4 | 4 | 4 | 4 | 1 | 4 | 0 | 0 | 2 | 2 |  |  |  |
|  | 1 | 4 | 4 | 4 | 4 | 4 | 4 | 4 | 4 | 0 | 3 | 0 | 0 | 1 | 2 |  |  |  |
| 42 | 3 | 3 | 4 | 3 | 4 | 4 | 4 | 2 | 2 | — | 1 | 0 | 0 | 3 | 0 |  |  |  |
|  | 1 | 0 | 4 | 3 | 3 | 4 | 4 | 1 | 0 | 0 | 0 | 0 | 0 | 0 | 0 |  |  |  |
| 43 | 3 | 4 | 4 | 4 | 3 | 2 | 4 | 4 | 4 | 0 | 4 | 1 | 1 | 4 | 2 |  |  |  |
|  | 1 | 4 | 3 | 3 | 2 | 2 | 4 | 2 | 4 | 0 | 2 | 0 | 0 | 3 | 1 |  |  |  |
| 44 | 3 | 4 | 4 | 4 | 4 | 4 | 4 | 4 | 3 | 4 | 3 | 0 | 0 | 3 | 0 |  |  |  |
|  | 1 | 4 | 4 | 3 | 2 | 4 | 4 | 0 | 3 | 0 | 3 | 0 | 0 | 2 | 0 |  |  |  |
| 45 | 3 | 4 | 4 | 3 | 2 | — | 4 | 4 | 4 | 0 | 0 | 0 | 0 | 0 | 1 |  |  |  |
|  | 1 | 4 | 4 | 3 | 1 | — | 4 | 4 | 4 | 0 | 0 | 0 | 0 | 0 | 0 | 0 |  |  |
| 46 | 3 | 4 | 4 | 3 | 2 | — | 4 | 4 | 0 | 0 | 2 | 0 | 0 | 2 | 0 |  |  |  |
|  | 1 | 3 | 4 | 4 | 2 | — | 4 | 3 | 0 | 0 | 1 | 0 | 0 | 1 | 0 |  |  |  |
| 47 | 3 | 4 | 4 | 3 | 1 | 4 | 4 | 3 | 2 | 1 | 3 | 0 | 0 | 0 | 1 |  |  |  |
|  | 1 | 4 | 4 | 1 | 0 | 4 | 4 | 1 | 0 | — | 2 | 0 | 0 | 0 | 1 |  |  |  |
| 48 | 3 | 4 | 4 | 4 | 4 | 4 | 4 | 3 | 1 | 0 | 0 | 0 | 0 | 3 | 0 |  |  |  |
|  | 1 | 0 | 4 | 1 | 4 | 4 | 4 | 1 | 0 | 0 | 0 | 0 | 0 | 2 | 0 |  |  |  |
| 49 | 3 | 4 | 4 | 3 | 2 | 4 | 4 | 3 | 2 | 0 | 1 | 0 | 0 | 1 | 0 |  |  |  |
|  | 1 | 4 | 4 | 3 | 2 | 4 | 4 | 1 | 1 | 0 | 0 | 0 | 0 | 0 | 0 |  |  |  |
| 50 | 3 | 1 | 4 | 2 | 4 | 4 | 4 | 2 | 1 | 0 | 1 | 0 | 0 | 1 | 0 |  |  |  |
|  | 1 | 1 | 4 | 1 | 4 | 0 | 3 | 0 | 0 | 0 | 0 | 0 | 0 | 0 | 0 |  |  |  |
| 51 | 3 | 4 | 4 | 4 | 4 | 4 | 4 | 3 | 4 | 0 | 2 | 0 | 0 | 1 | 0 |  |  |  |
|  | 1 | 2 | 4 | 2 | 3 | 4 | 4 | 1 | 1 | 0 | 0 | 0 | 0 | 1 | 0 |  |  |  |
| 52 | 3 | 4 | 4 | 3 | 1 | 4 | 4 | 4 | 4 | 1 | 1 | 0 | 0 | 3 | 1 |  |  |  |
|  | 1 | 4 | 4 | 3 | 0 | 4 | 4 | 3 | 2 | 0 | 1 | 0 | 0 | 1 | 0 |  |  |  |
| 53 | 3 | 4 | 4 | 4 | 4 | 0 | 4 | 4 | 4 | 4 | 3 | 0 | 0 | 1 | 0 |  |  |  |
|  | 1 | 4 | 3 | 4 | 3 | 4 | 4 | 0 | 3 | 0 | 2 | 0 | 0 | 0 | 0 |  |  |  |
| 54 | 3 | 4 | 4 | 4 | 2 | — | 4 | 0 | 2 | 0 | 1 | 0 | 0 | 0 | 0 |  |  |  |
|  | 1 | 4 | 0 | 4 | 0 | 4 | 4 | 0 | 0 | 0 | 0 | 0 | 0 | 0 | 0 |  |  |  |
| 55 | 3 | 3 | 4 | 2 | 0 | 4 | 4 | 4 | 3 | 3 | 2 | 0 | 0 | 3 | 2 |  |  |  |
|  | 1 | 1 | 4 | 1 | 0 | 4 | 4 | 1 | 1 | 0 | 2 | 0 | 0 | 3 | 1 |  |  |  |

-continued

Post-Emergent Phytotoxicity Results
Plant Species

| Compound No. | Rate (lb/A.) | Cockle burr | Lambs-quarter | Morning-glory | Pigweed | Wild Buckwheat | Wild Mustard | Alfalfa | Cotton | Peanut | Soybean | Corn | Grain Sorghum | Rice | Wheat | Oats | Radish | Sugar beets |
|---|---|---|---|---|---|---|---|---|---|---|---|---|---|---|---|---|---|---|
| 56 | 3 | 4 | 4 | 1 | 0 | 4 | 4 | 0 | 2 | 1 | 4 | 0 | 0 | 1 | 1 | | | |
|  | 1 | 3 | 4 | 1 | 0 | 4 | 4 | 0 | 1 | 0 | 1 | 0 | 0 | 1 | 1 | | | |
| 57 | 3 | 4 | — | 4 | 1 | 4 | 4 | 1 | 0 | 0 | 2 | 0 | 0 | 0 | 0 | | | |
|  | 1 | 4 | 4 | 1 | 0 | 2 | 4 | 1 | 0 | — | 2 | 0 | 0 | 0 | 0 | | | |
| 58 | 3 | 4 | 4 | 4 | 2 | 4 | 4 | 4 | 4 | 1 | 4 | 0 | 1 | 1 | 1 | | | |
|  | 1 | 4 | 4 | 3 | 1 | 4 | 4 | 2 | 4 | 1 | 2 | 0 | 0 | 0 | 0 | | | |
| 59 | 3 | 4 | 4 | 4 | 2 | 4 | 4 | 3 | 4 | 1 | 3 | 1 | 4 | 2 | 4 | | | |
|  | 1 | 4 | 4 | 4 | 1 | 3 | 4 | 1 | 1 | 0 | 1 | 0 | 0 | 0 | 1 | | | |
| 60Z | 3 | 4 | 4 | 4 | 1 | 4 | 4 | 2 | 2 | 1 | 2 | 0 | 0 | 1 | 2 | | | |
|  | 1 | 4 | 4 | 3 | 0 | 4 | 4 | 1 | 1 | 0 | 1 | 0 | 0 | 0 | 0 | | | |
| 61 | 3 | 4 | 4 | 3 | 4 | 4 | 4 | 2 | 4 | 1 | 3 | 0 | 0 | 0 | 0 | | | |
|  | 1 | 3 | 4 | 1 | 4 | 3 | 4 | 1 | 2 | 1 | 3 | 0 | 0 | 0 | 0 | | | |
| 62 | 3 | 4 | 4 | 4 | 4 | 4 | 4 | 3 | 1 | 0 | 4 | 0 | 0 | 2 | 2 | | | |
|  | 1 | 0 | 4 | 0 | 3 | 2 | 4 | 3 | 0 | 0 | 1 | 0 | 0 | 0 | 0 | | | |
| 63 | 3 | 4 | 4 | 2 | 2 | 3 | 3 | 4 | 0 | 0 | 3 | 0 | 0 | 0 | 0 | | | |
|  | 1 | — | 4 | 1 | 1 | 0 | 1 | 1 | 0 | 0 | 2 | 0 | 0 | 0 | 0 | | | |
| 64 | 3 | 3 | 4 | 3 | 2 | 4 | 4 | 2 | 3 | 1 | 2 | 0 | 0 | 1 | 3 | | | |
|  | 1 | 0 | 4 | 0 | 1 | 2 | 2 | 1 | 1 | 0 | 1 | 0 | 0 | 0 | 1 | | | |
| 65 | 3 | 4 | 4 | 3 | 4 | 4 | 4 | 3 | 4 | 0 | 3 | 1 | 2 | 1 | 4 | | | |
|  | 1 | 4 | 2 | 1 | 2 | 1 | 4 | 1 | 1 | 0 | 2 | 0 | 0 |  | 2 | | | |
| 66 | 5 |  |  |  |  |  | 1 |  |  |  |  |  |  |  |  | 2 | 2 | 4 |
| 67 | 5 |  |  |  |  |  | 3 |  |  |  |  |  |  |  |  | 3 | 4 | 4 |
| 68 | 5 |  |  |  |  |  | 2 |  |  |  |  |  |  |  |  | 2 | 4 | 3 |
| 69 | 5 |  |  |  |  |  | 2 |  |  |  |  |  |  |  |  | 3 | 4 | 4 |
| 70 | 5 |  |  |  |  |  | 1 |  |  |  |  |  |  |  |  | 3 | 4 | 4 |

The method of selectively combating unwanted vegetation according to this invention comprises the step of applying to the unwanted vegetation an effective amount of a compound having the general structural formula

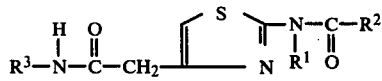

in which $R^1$ is hydrogen or lower alkyl, $R^2$ is amino, lower alkyl, lower chloroalkyl, lower alkylamino, lower alkenylamino, lower alkoxy or $C_3$ to $C_5$ cycloalkyl and $R^3$ is phenyl, thiazolyl, thiadiazolyl or lower alkyl-substituted, halogen-substituted or trifluoromethyl-substituted phenyl, thiazolyl or thiadiazolyl. The test results disclosed above serve to illustrate the selectivity and efficacy of the novel herbicides, so that a choice can be made of the compound and rate of application to suit a specific weed problem in a particular crop. The method is particularly desirable for combating broad-leaved weeds in peanuts, corn, grain sorghum and wheat crops. It will be understood that a final selection of application rates is best made after outdoor tests under the conditions of application, soil and climate which will actually be encountered in the field. In general, outdoor application is done less efficiently than under the controlled conditions of a greenhouse laboratory and so somewhat higher rates of application are required.

I claim:

1. The selectively phytotoxic 2-acylaminothiazol-4-ylacetamide compound having the general structural formula

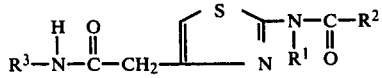

in which $R^1$ is hydrogen or lower alkyl, $R^2$ is amino, lower alkyl, lower chloroalkyl, lower alkylamino, lower alkenylamino, lower alkoxy or $C_3$ to $C_5$ cycloalkyl and $R^3$ is phenyl, methoxyphenyl, chlorophenyl, bromophenyl, fluorophenyl, iodophenyl, or lower alkyl-substituted or trifluoromethyl-substituted phenyl, thiazolyl or thiadiazolyl.

2. The compound as claimed in claim 1 in which $R^1$ is hydrogen, $R^2$ is ethyl and $R^3$ is phenyl.

3. The compound as claimed in claim 1 in which $R^1$ is hydrogen, $R^2$ is isopropyl and $R^3$ is 3,4-dichlorophenyl.

4. The compound as claimed in claim 1 in which $R^1$ is hydrogen, $R^2$ is tert-butyl and $R^3$ is 3,4-dichlorophenyl.

5. The compound as claimed in claim 1 in which $R^1$ is hydrogen, $R^2$ is ethyl and $R^3$ is m-trifluoromethylphenyl.

6. The compound as claimed in claim 1 in which $R^1$ is hydrogen, $R^2$ is cyclopropyl and $R^3$ is trifluoromethylphenyl.

7. The compound as claimed in claim 1 in which $R^1$ is hydrogen, $R^2$ is tert-butyl and $R^3$ is m-trifluoromethylphenyl.

8. The compound as claimed in claim 1 in which $R^1$ is hydrogen, $R^2$ is isopropyl and $R^3$ is m-trifluoromethylphenyl.

9. The compound as claimed in claim 1 in which $R^1$ is methyl, $R^2$ is methylamino and $R^3$ is m-trifluoromethylphenyl.

10. The compound as claimed in claim 1 in which $R^1$ is methyl, $R^2$ is propylamino and $R^3$ is m-trifluoromethylphenyl.

11. The compound as claimed in claim 1 in which $R^1$ is hydrogen, $R^2$ is methyl and $R^3$ is 4-methyl-2-thiazolyl.

12. The compound as claimed in claim 1 in which $R^1$ is hydrogen, $R^2$ is 2-methylpropyl and $R^3$ is m-trifluoromethylphenyl.

13. The compound as claimed in claim 1 in which $R^1$ is hydrogen, $R^2$ is isopropyl and $R^3$ is m-iodophenyl.

* * * * *

UNITED STATES PATENT AND TRADEMARK OFFICE
CERTIFICATE OF CORRECTION

PATENT NO. : 4,152,329
DATED : May 1, 1979
INVENTOR(S) : Roger P. Cahoy

It is certified that error appears in the above-identified patent and that said Letters Patent are hereby corrected as shown below:

Column 7, Compound 24, under heading $R^2$ should read "methylamino", under heading $R^3$ should read "3,4-dichlorophenyl", under heading M.P.(°C.) should read "188-191".

Column 9 and 10, Table of Post-Emergent Phytotoxicity Results,
Compound No. 2, 1 (lb/A), under heading Cotton --0-- should be added.
Compound No. 7, 3 (lb/A), under heading Rice --1-- should be added.
Compound No. 14, 1 (lb/A), under heading Alfalfa --4-- should be added.
Compound No. 17, 3 (lb/A), under headings Grain Sorghum, Rice and Wheat the numbers --0--, --2-- and --0-- should appear in that order.

Column 11 and 12, Compound No. 45, the "0" under Oats should be removed.
Compound No. 50, 3 (lb/A), under heading Peanuts --0-- should be added.

Column 13 and 14, Compound No. 60Z should read "60".
Compound No. 65, 1 (lb/A), under heading Rice --0-- should be added.

Signed and Sealed this

Twenty-ninth Day of January 1980

[SEAL]

Attest:

SIDNEY A. DIAMOND

Attesting Officer    Commissioner of Patents and Trademarks